United States Patent [19]

Raible

[11] 4,297,318

[45] * Oct. 27, 1981

[54] BLOOD OXYGENATOR

[75] Inventor: Donald A. Raible, Santa Ana, Calif.

[73] Assignee: Bentley Laboratories, Inc., Irvine, Calif.

[*] Notice: The portion of the term of this patent subsequent to May 19, 1998, has been disclaimed.

[21] Appl. No.: 54,268

[22] Filed: Jul. 2, 1979

Related U.S. Application Data

[63] Continuation-in-part of Ser. No. 823,149, Aug. 9, 1977, which is a continuation-in-part of Ser. No. 689,971, May 26, 1976, Pat. No. 4,268,476, which is a continuation-in-part of Ser. No. 584,464, Jun. 6, 1975, abandoned, and a continuation-in-part of Ser. No. 689,971.

[51] Int. Cl.$^3$ .............................................. A61M 1/03
[52] U.S. Cl. ................................ 422/46; 128/DIG. 3; 261/DIG. 28; 422/47
[58] Field of Search ............ 422/46, 47; 128/DIG. 3; 435/2; 261/DIG. 28

[56] References Cited

U.S. PATENT DOCUMENTS

| | | | |
|---|---|---|---|
| 2,934,067 | 4/1960 | Calvin | 422/47 |
| 3,468,631 | 9/1969 | Raible et al. | 422/46 |
| 3,615,238 | 10/1971 | Bentley | 422/46 |
| 3,898,045 | 8/1975 | Bowley | 422/47 |
| 4,065,264 | 12/1977 | Lewin | 422/46 |

Primary Examiner—Michael S. Marcus
Attorney, Agent, or Firm—Lyon & Lyon

[57] ABSTRACT

A blood oxygenating device comprising an oxygenating chamber and a heat exchange chamber, the oxygenating chamber comprising a bubbler chamber and a mixing chamber. Oxygen is introduced into the bubbler chamber through a porous diffusion means situated near the inlet of the bubbler chamber. Bubbles pass from the bubbler chamber into the mixing chamber which is provided with a plurality of secondary flow-producing deflectors to promote secondary flow and rotation of blood bubbles passing therethrough. The secondary flow results in a highly efficient oxygen-carbon dioxide transfer. The blood bubbles are then passed through a heat exchange chamber and a defoaming means prior to exiting the oxygenating device.

In a preferred version, blood and oxygen-rich gas are admitted at the top of the device and caused to flow substantially downwardly through a tortuous path which causes at least a portion of the blood bubbles to rotate. During the course of downward flow, the blood-gas-bubble mixture passes around a heat exchange device, which preferably is convoluted, helically wound tubing so as to form the tortuous path, to bring the blood to a desired temperature. The oxygenator is equipped with a defoaming means such that the blood bubbles are converted back into liquid blood, which is then returned to the patient. Vent means are provided for removal of carbon dioxide and other vent gases. Means for promoting secondary flow in the blood are preferably provided in the upward region of the oxygenator.

18 Claims, 13 Drawing Figures

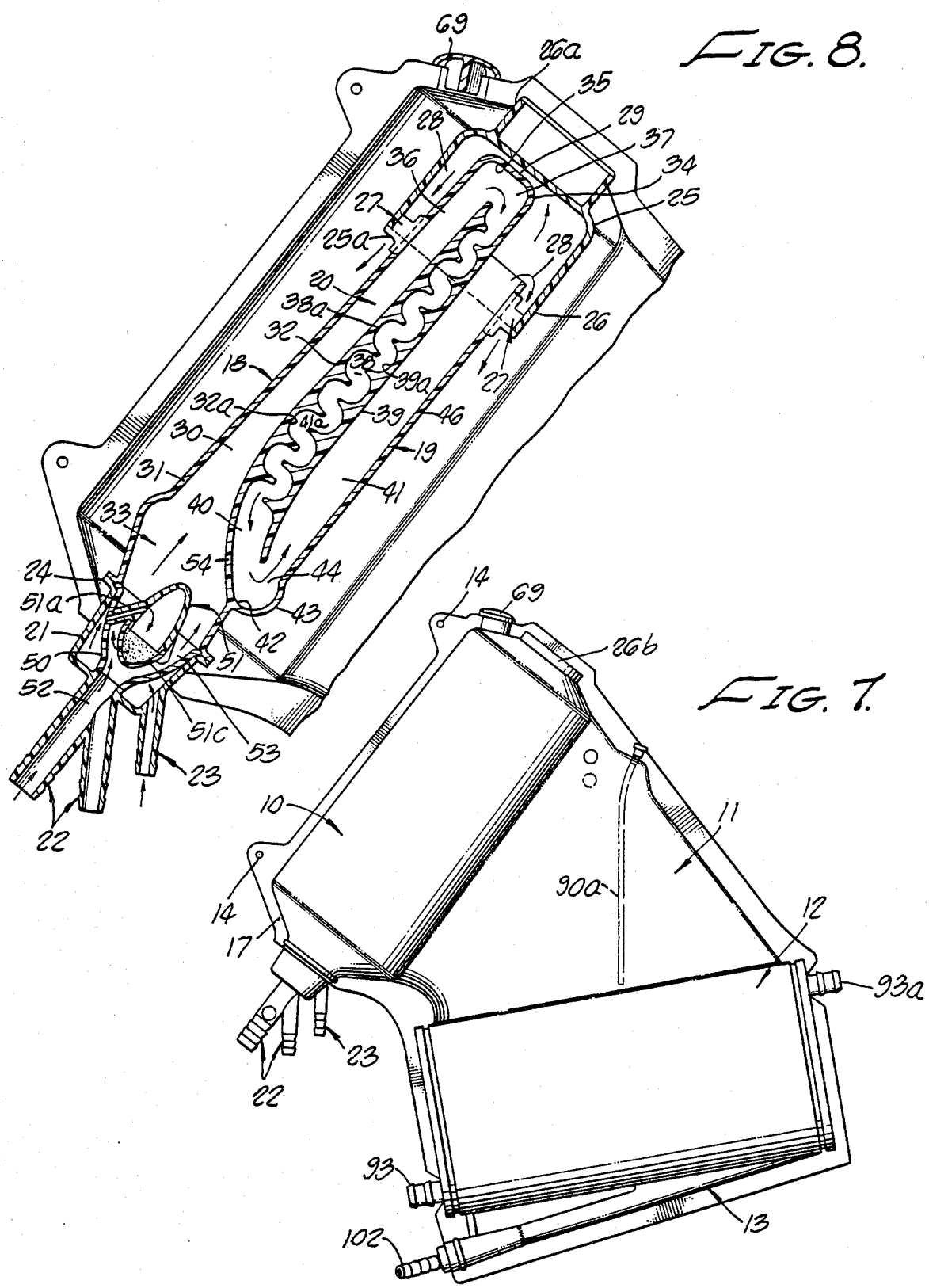

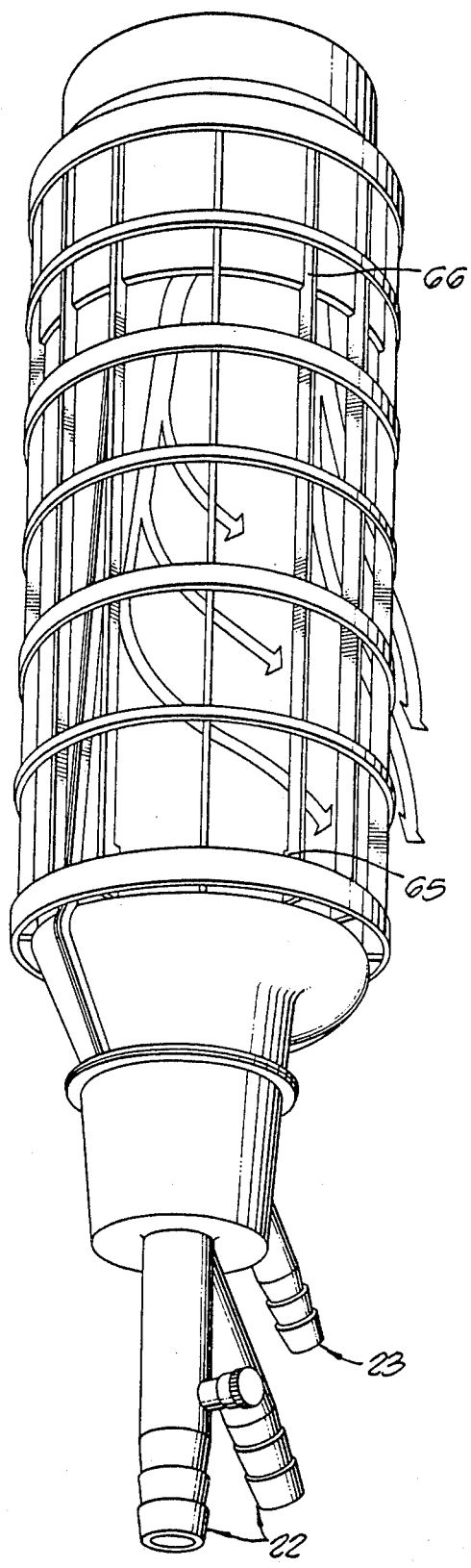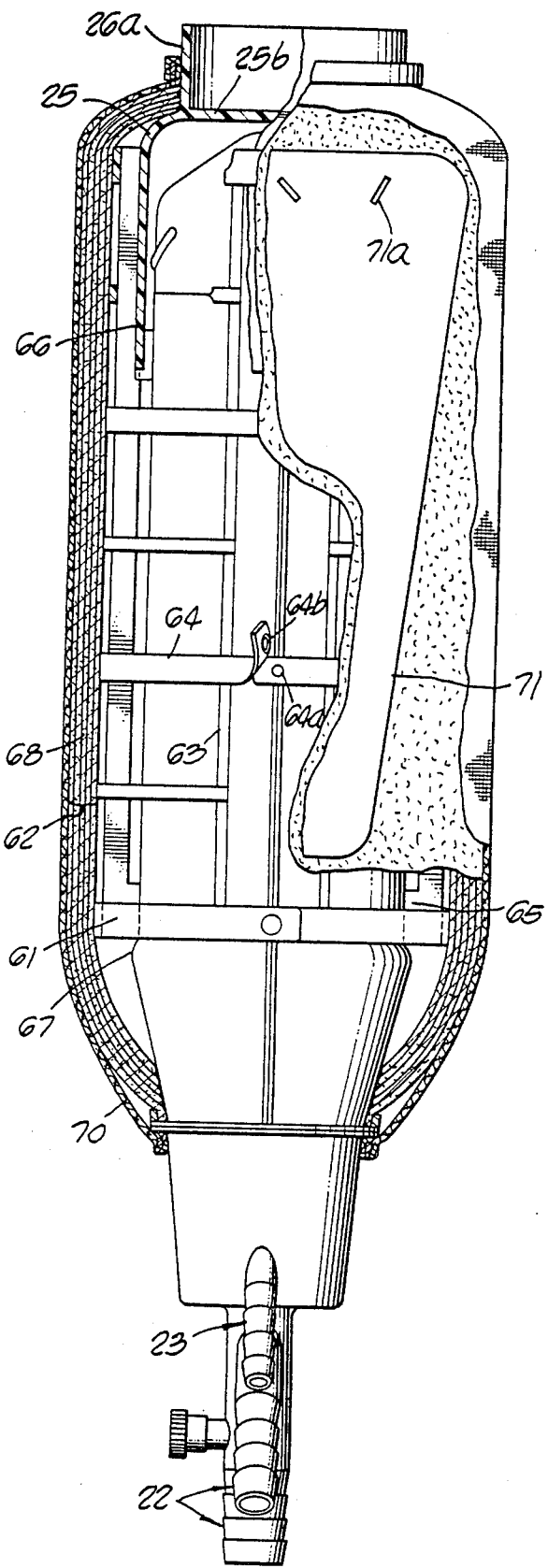

BLOOD OXYGENATOR

RELATED APPLICATIONS

This application is a continuation-in-part of Ser. No. 823,149 filed on Aug. 9, 1977, which is a continuation-in-part of my copending application Ser. No. 689,971, filed May 26, 1976, now U.S. Pat. No. 4,268,476, which in turn is a continuation-in-part of my application Ser. No. 584,464, filed June 6, 1975, now abandoned. This application is also a continuation-in-part of application Ser. No. 689,971. Each of these applications is incorporated herein by this reference.

BACKGROUND OF THE INVENTION

The invention herein relates to a method for oxygenating blood and to a bubble-type oxygenator of the kind used in thoracic surgery, and more particulary to an oxygenator having improved bubble formation and improved oxygen-carbon dioxide exchange.

The history of safe and reliable blood oxygenators is relatively brief. Such oxygenators are used in open-heart surgery and other operations and treatments of the body when it is necessary to establish an extracorporeal circulation system for temporarily assuming the functions of the heart and lungs of the patient. In such a system, the oxygenator operates to perform the function usually performed by the lungs of the patient, i.e., the life-supporting transfer of oxygen into the blood and carbon dioxide out of the blood. The oxygenator is used in association with a pump which performs the function of the heart to cause circulation of the blood. Thus, early versions of the oxygenator were often referred to as "heart-lung" machines. The early heart-lung machines were typically rotating discs which passed through a pool of blood, but were only partially immersed therein such that the free surface of the disc exposed the blood to oxygen and accomplished some gas transfer. After this, bag-type oxygenators were introduced which were superior to the disc oxygenators, but which left much to be desired.

A major advance occurred in the mid-1960's when the rigid (or hard shell) bubble oxygenator was developed. The history of such oxygenators had its beginnings in the device shown in Raible, et al, U.S. Pat. No. 3,468,631, which is incorporated herein by reference, and they first came into clinical use with the development of the devices shown in Bentley et al, U.S. Pat. Nos. 3,488,158 and 3,578,411 which have come to be known as the Bentley Oxygenator. At the present time, such oxygenators are used more frequently than any other type. Among the important features of the oxygenators disclosed in the foregoing patents was the provision of a self-contained heat exchanger.

In the intervening years, some relatively minor modifications have been made in bubble oxygenators, e.g., those disclosed in Brumfield U.S. Pat. Nos. 3,764,271 and 3,769,162. However, all rigid bubble oxygenators shown in the aforesaid patents and all other such oxygenators known to applicant to have been put to actual clinical use have had one fundamental feature in common, namely, each of them introduced blood and oxygen-rich gas in the lower region of the device and caused a column of bubbles to flow upwardly through the initial portion of the device. Bentley, et al, U.S. Pat. Nos. 3,488,158 and 3,578,411 and the aforesaid Brumfield patents do have some downward portions in the flow path of the gas blood mixture, but it is clear that they were designed to provide for initial upward flow of the gas and blood mixture in that portion of the flow path where the bubbles are formed. In addition, Fields U.S. Pat. No. 3,204,631, discloses an oxygenator in which blood enters at an upper portion and oxygen enters at a lower portion such that there is a counter-flow relationship with the blood initially flowing downwardly and the oxygen flowing upwardly.

The present invention is a further improvement of the device shown in the Bentley U.S. Pat. No. 3,615,238, issued Oct. 26, 1971, entitled "Oxygenator"; the Bentley, et al, U.S. Pat. No. 3,578,411 issued May 11, 1971, entitled "Bubbler Assembly for Blood Treating Apparatus"; the Bentley, et al U.S. Pat. No. 3,488,158 issued Jan. 6, 1970, entitled "Bubbler Assembly for Oxygenator"; and applications, Ser. Nos. 436,913, now abandoned, and 565,043, now U.S. Pat. No. 4,058,369 titled "Blood Oxygenator" and "An Improved Oxygenating Device", respectively, the disclosures of which are incorporated by reference herein. These devices each represent important developments in the blood treatment art. However, since these devices temporarily assume the function of the heart and lungs of a patient during certain operations or other treatments of the body, further improvements are desired which will effect within such devices a blood treatment process as equivalent as possible to that natural process effected by the heart and lungs.

One aspect of the human oxygenating process which has heretofore been difficult to duplicate concerns the ratio of oxygen in the blood to carbon dioxide commonly expressed as the physiological ratio of $pO_2$ to $pCO_2$. In the past, oxygenating devices were either unable to maintain this $pO_2$ to $pCO_2$ ratio or, in an effort to maintain such a ratio over the range of flow rates required during operation of the devices, have operated inefficiently and/or in a manner which may adversely affect the blood. For example, when an increase in $pO_2$ was desired, it could be effected only by a substantial increase in the flow of oxygen with respect to the flow of blood into the device. A high gas-to-blood-flow ratio represented an inefficient operation of the oxygenator and, more importantly, substantially increased the risk of hemolysis.

Therefore, there is a need for a method and a device for oxygenating blood whereby (a) oxygen to blood transfer can be effectively and efficiently achieved with an improved gas-to-blood flow rate and (b) improved blood and blood bubble flow characteristics can be obtained.

SUMMARY OF THE INVENTION

The present invention is directed to a method and an oxygenating device with the above features. The oxygenating device comprises an oxygenating chamber which comprises generally a bubble column, including a bubbler chamber and a mixing chamber. The mixing chamber is also referred to as a passageway or flow path. The bubbler chamber is provided with oxygen and blood inlet means. Venous blood is introduced to the bubbler chamber and is combined with oxygen containing gas to form a mixture of blood and gas, the mixture including blood bubbles. The mixture is then passed along the mixing chamber. The mixing chamber is provided with a plurality of secondary flow-producing means which function to rotate at least a portion of the blood bubbles passing therethrough.

In a particularly preferred embodiment, the gas and blood enter the oxygenator at the top or upward region thereof and both follow a downward path through substantially the entire flow path through the gas transfer portion of the oxygenator, where the path contains means for inducing rotation of the blood bubbles flow. This path is referred to as "tortuous" herein. A heat exchange device is placed in this downward path to bring the blood to the desired temperature. Preferably, this heat exchange device is a helically wrapped convoluted tube through which a heat exchange fluid passes and around which the blood-gas mixture passes. Thus, blood passes downwardly along the flow path, wherein at least a portion of the blood flows helically downward and the blood bubbles are rotated thereby. Means for imparting secondary flow to the blood-gas mixture and rotating the blood bubbles in the initial portion of their flow path preferably is also provided. The means for rotating the blood bubbles in the initial portion of the flow path preferably comprises an undulating path which is generally conical in shape. It has been found that a very high degree of gas transfer efficiency is achieved when the blood bubbles are rotated.

DESCRIPTION OF DRAWINGS

These and other features, aspects and advantages of the present invention will become better understood with reference to the following description, appended claims, and accompanying drawings where:

FIG. 7 is a side view of the oxygenating device of FIG. 6;

FIG. 8 is a side sectional view of the oxygenating chamber of the device of FIG. 6;

FIG. 9 is a perspective view of the oxygenating chamber and the defoamer support member of the device of FIG. 6 illustrating the flow of blood and blood bubbles from the outlet of the chamber;

FIG. 10 is a view of the oxygenating chamber of the device of FIG. 6 illustrating the placement of the defoamer support member and splash shield;

DESCRIPTION

Figure 1:
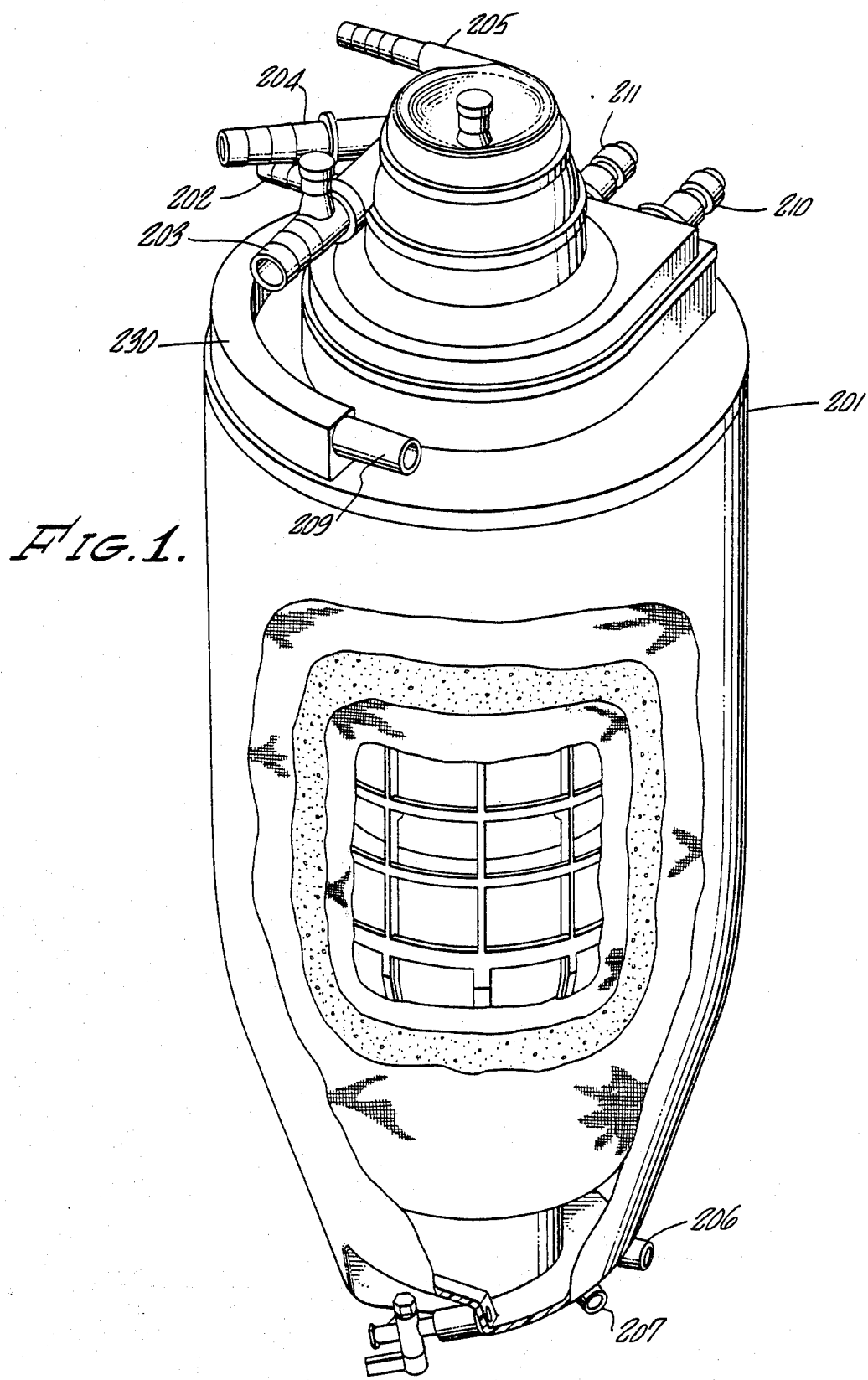
FIG. 1 is a perspective view of a preferred oxygenator of the present invention.
Figure 2:
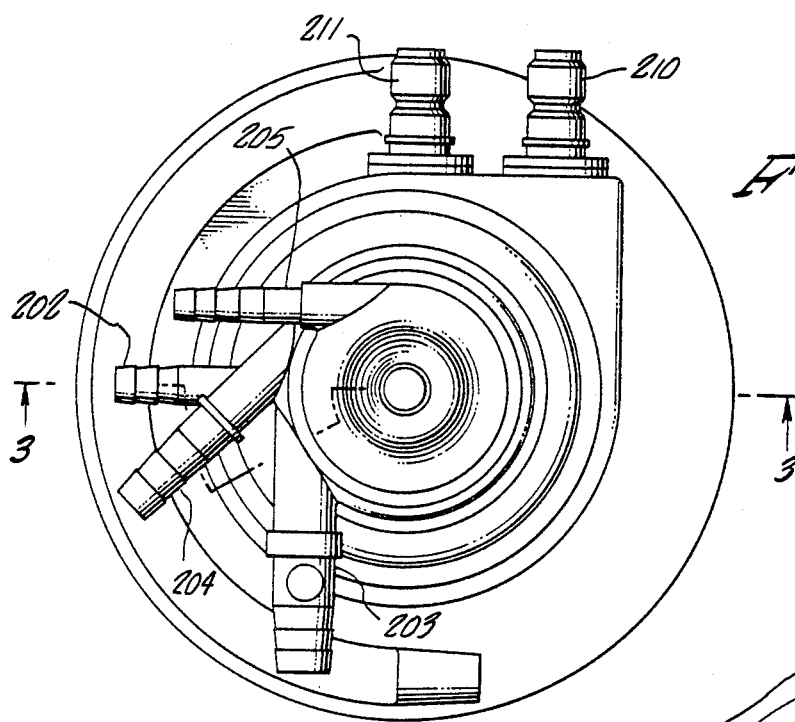
FIG. 2 is a top view of the oxygenator of FIG. 1.

As described in detail hereinbelow, oxygenators having features of the present invention enable improved blood bubble formation and blood bubble flow which result in substantial improvement of the oxygenating capabilities of the oxygenator. In particular, such an oxygenator provides for improved flow of blood bubbles along the passageway within the oxygenating chamber as well as improved blood bubble formation. Such improved flow and bubble formation avoid the situation in which relatively few nonuniform blood bubbles are initially generated and then not adequately mixed with the free oxygen to effectuate optimum oxygen-carbon dioxide transfer without harm to the blood.

Furthermore, an oxygenator as described herein has an improved structure such that the volume of priming liquid for start-up of oxygenating device can be substantially reduced. This reduction is advantageous in the commonly occurring situations where either blood (not that of the patient) alone, blood mixed with a solution for hemo-dilution, or hemo-dilution solution alone is used for priming the oxygenator. The reason why such reduction is advantageous in the first situation mentioned above, i.e., when blood (not that of the patient) alone is used as priming liquid, is that the less liquid used which is not the blood of the patient, the more physically acceptable is the oxygenating process to the patient. The reason for the advantage in the second situation, i.e., when blood mixed with a solution for hemo-dilution is used as priming liquid, is the one just mentioned, as well as the fact that blood alone is more readily oxygenated than is blood mixed with hemo-dilution solution because of reduced hematocrit of the latter. Therefore, the less mixture used for priming, the better the oxygenating during the initial operation stages. The reasons for the advantage in the third situation, i.e., when hemo-dilution solution alone is used as priming liquid, are the same as those mentioned above for the second.

FIGS. 1-5 show a particularly preferred embodiment of the present invention. In this version, the oxygenator, which is generally cylindrical in configuration, comprises an outer shell 201 which is provided with a gas inlet 202 and blood inlets 203 and 204. Inlet 205 is provided for priming as well as for optimal medication administration and, if needed, as a return inlet from a cardiotomy reservoir. Blood outlets 206 and 207 and gas vent 209 are also provided. An inlet 210 and an outlet 211 for heat exchanger fluid are also provided.

Figure 4:
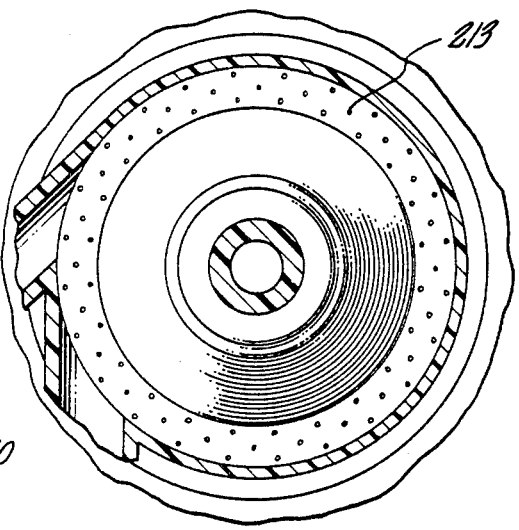
FIGS. 4 and 5 are transverse sections of the oxygenator of FIG. 1 taken along lines 4—4 and 5—5, respectively, in FIG. 3.

Referring to FIG. 4, the internal construction of the oxygenator is shown in more detail. AS there depicted, gas inlet 202 connects with annular chamber 212 which is bounded on its upper end by diffusion means 213. This diffusion means may be any suitable porous or perforated apertured member, but preferably is a perforated member. This perforated diffusion member does not constitute part of the present invention, but rather is a separate invention which is assigned to the assignee of the present application. In its preferred form the diffusion means has three circular patterns containing 66 perforations which are 0.010 inches in diameter and 6 perforations which are 0.025 inches in diameter, the larger perforations being more or less uniformly distributed among the smaller perforations.

Blood inlet means 203 and 204 connect with the interior of the annular chamber 214 is a generally tangential manner. Thus, when chamber 214 is filled with blood, flowing in a spiral manner, and oxygen containing gas is admitted to the device through inlet 202, the gas, such as oxygen or an oxygen-rich mixture, passes through inlet 202, into chamber 212 and through diffusion means 213 into the body of blood in chamber 214. As will be described in more detail below, bubbles are formed in chamber 214 when the gas enters the blood.

Chamber 214 connects with annular channel 215 and undulating distribution channel 216, the latter being conical in general shape. Channel 216 connects with annular mixing chamber 217 which is provided with heat exchange tubing 218 and which contains a descending flow path for the blood. Heat exchange tubing 218 is a convoluted tubing having a large diameter portion 219 and a small diameter portion 220. Thus, although heat exchange tubing has a large diameter 219 which is essentially the same dimension as the radial distance between inner wall 221 and outer wall 222 of the mixing chamber, there are a plurality of descending flow paths between the walls of the mixing chamber and the walls of tubing 218 formed by the convolution. In addition, since tubing 218 is helically wrapped around inner wall 221, there is a helically descending flow path through the mixing chamber.

At the lower end of chamber 217, outer wall 222 terminates approximately two-thirds of the distance from the top to the bottom of the oxygenator to permit the bubbles of blood to come into contact with defoaming means 223. Thus the elevation of the blood outlets 206 and 207 is lower than the bottom of the tortuous flow path through the mixing chamber. While several defoaming means may be used, e.g., that disclosed in U.S. Pat. No. 3,468,631, it is preferred to form defoaming material 223 from a polyurethane foam having about ten to thirty pores per inch. The polyurethane foam is coated with a silicone defoaming agent. Optionally, a spacer 225 may be provided between defoaming material 223 and wall 222. Spacer 225 may comprise a ribbed structure which provides open spaces therebetween.

Open spaces 226 are provided in space 225 which permit blood to come into contact with defoaming material 223. The lower end of the oxygenator is provided with reservoir 229 where liquid blood is collected.

Annular passage 230 connects with vent means 209 so that vent gases may be exhausted from the oxygenator. A mesh sleeve 231 which may be polyester, polypropylene, polyethelene, nylon or other suitable fabric is positioned around defoaming material 223 and is provided with elastic banks 232 to hold it in place. Port 205 connects with chamber 235 which, in turn, connects with conduit 236. Port 205 is used for priming the oxygenator and may also be used for addition of medication to the blood or for blood coming from a cardiotomy reservoir.

Figure 5:
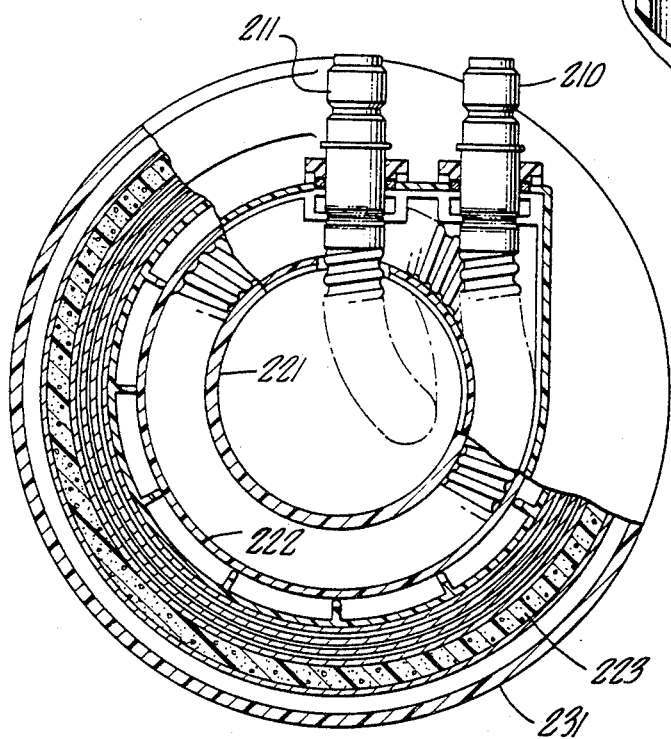
Figure 3:
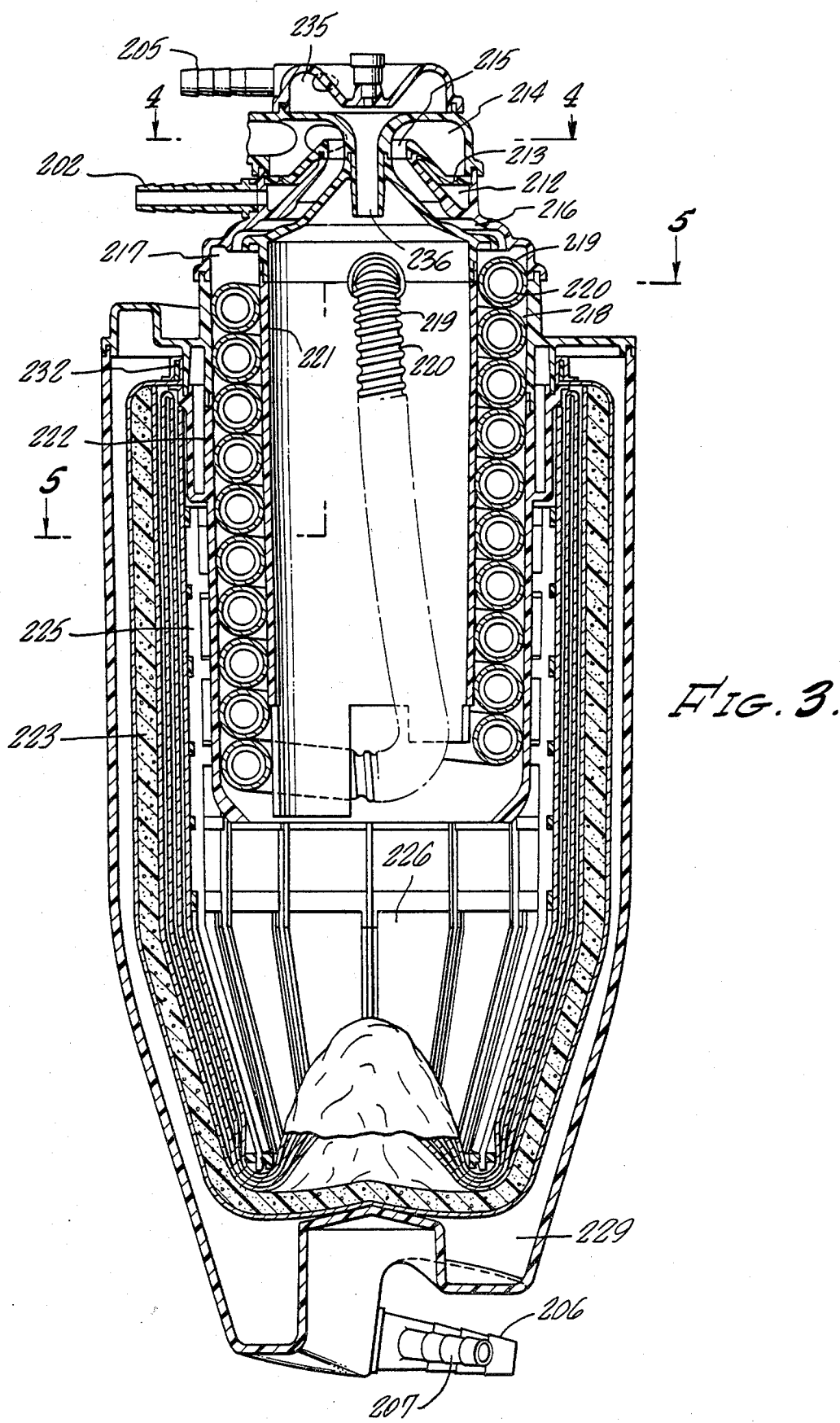
FIG. 3 is a cross sectional view of the oxygenator of FIG. 1 taken along line 3—3 in FIG. 2.

FIGS. 4 and 5 further illustrate the internal structure of the oxygenator of FIG. 1.

It is to be understood that the present invention is not to be limited to any particular theory of operation. However, in an effort to provide as complete a disclosure as possible of the mode of operation of the present invention, the description which follows is believed to be accurate on the basis of present information. Even if future information were to demonstrate that the understanding of the invention which presently exists is incomplete or inaccurate in some respect, one essential fact would remain unchanged, namely, the apparatus and method of the present invention achieve a significant step forward in blood oxygenation technology. The key feature in this forward step which results in increased efficiency both with regard to gas transfer during oxygenation and in heat exchange is the combination of the substantially concurrent downward flow path of the blood-gas mixture with the secondary flow which occurs in that path. In addition, the location of the heat exchange in this downward path is of substantial significance.

In operation of oxygenator of FIG. 1, oxygen enters through port 202 and passes through passageway 212 and perforated member 213. The oxygen then mixes with blood entering through ports 203 and 204 and the mixture flows in a spiral direction through chamber 214 and into passage 215 and then into conical passage 216 which has an undulating cross section. This undulating cross section promotes secondary flow and the bubbled blood is spread outwardly and down into bubble column 217 where it continues to flow downwardly through two primary flow paths. First, since heat exchanger tubing 218 is convoluted, there is a more or less vertically downward path through the convolutions. Second, there is a helically downward path generally parallel to the path defined by the helically coiled heat exchanger tubing. These primary flow paths are also influenced by the flow deflection caused by heat exchanger tubing 218 itself. Thus, the bubbled gas-blood mixture flows substantially downwardly, but is influenced by a variety of factors such that effective mixing of the gas with the blood is promoted by reason of repeated twists and turns in the downward path taken by the blood-gas mixture. It is believed that the bubbles are rotated as they follow this path and that they are caused to change shape from generally spherical to elongated ellipsoidal and back again.

In this regard, it should be noted that when the blood-gas mixture passes through conical chamber 216, there is some reduction in pressure from the top of the chamber 216 to near atmospheric pressure when discharged at the top of bubble column 217. Thus, the size of the bubbles in chamber 216 generally increases as the blood-gas mixture flows through that chamber.

Preferably, the external convolutions on the heat exchange tubing 218 are also present on its internal wall as well to promote turbulent flow of the fluid, e.g., water, passing through heat exchange tubing 218 to provide increased heat transfer efficiency. Furthermore, it is believed that as the blood bubble mixture flows over the convoluted heat exchanger tubing, a thin film of blood is caused to cover the surface of the tubing due to surface tension. As further supplies of bubbled blood come into contact with the blood covering the heat exchanger tubing surface, the film becomes too thick and heavy to remain on the surface of the heat exchanger tubing and the now-warmed blood film runs from the surface of the convoluted tubing and is either re-bubbled with the free oxygen present or continuous to run as a liquid down through the bubble column. Thus, a type of filming heat exchange is believed to take place in which the velocity components of gravitational flow and of the pressure exerted by the incoming blood-gas mixture are both in a downward direction and, hence, are additive. It is believed that this combination of circumstances, which is believed to be unique to the present invention, has a significant effect in increasing the efficiency of heat exchange in the present invention.

The mechanism of gas exchange in bubble oxygenators is the subject of several theories and it is entirely possible that different mechanisms predominate in different designs of bubble oxygenators. It is believed that when oxygen comes in contact with the incoming blood in chamber 214, oxygen bubbles are formed in blood and that these bubbles become covered with plasma and red cells. It is believed that the oxygen is then transferred through the membrane of the red cell and into the hemoglobin where biologic gas transfer takes place, such that oxygen enters the blood and carbon dioxide is released.

Thus, gas exchanged is believed to be accomplished in conical chamber 216 and in mixing chamber 217 after which the blood bubbles flow through the defoamer material previously described. The oxygenated, defoamed liquid blood is then removed from the oxygenator and returned to the patient. Excess oxygen and carbon dioxide gases are vented upwardly and out of the top of the housing.

Among the important advantages of the version of the invention shown in FIG. 1 is the minimization and possible elimination of reverse blood flow, i.e., the phenomenon which occurs in all bubble oxygenators known to applicant in which upwardly traveling blood bubbles break and liquid blood flows downwardly back toward the point where oxygen is introduced such that some blood has a substantially longer residence time in the bubble column than other blood. Reverse flow is disadvantageous because the risk of blood damage by reason of repeated bubbling and breaking of the bubbles for an extended time exists and because the patient is deprived of a portion of his blood for a time longer than that required to accomplish oxygenation. Furthermore, the oxygenator of FIG. 1 permits zero retention of the patient's blood volume after the surgical procedure and requires a smaller amount of blood to be in the oxygenator at any given time. Similarly, the oxygenator is less sensitive to variations in gas flow rate than oxygenators requiring upward flow. Still further, the oxygenator of FIG. 1 eliminates the need to increase the venous pressure to cause upward vertical venous blood flow against gravitational forces in order to operate the device as is necessary in all clinically used bubble oxygenators known to applicant.

These advantages, taken with the substantially increased efficiency of the oxygenator of FIG. 1 in accomplishing gas transfer and heat exchange means that an oxygenator of the present invention gives better and safer blood oxygenation than has hitherto been available. In this regard, the rounded surfaces which define the travel path of the blood-gas mixture do not cause blood damage in the manner of sharp corners and thus also help to decrease the possibility of blood damage.

Other advantages, it is believed, of the present invention will be apparent to those skilled in the art. Thus, the present disclosure provides a description of the nature of the present invention and useful information with regard to its operational characteristics, and a statement of some of the advantages believed to be inherent therein.

Referring now in detail to FIGS. 6-11 there is shown an alternate embodiment of the oxygenating device according to the present invention. The device comprises an upper cylindrical chamber, generally designated 10 (commonly called an oxygenating chamber), a narrow central chamber, generally designated 11, and a lower cylindrical chamber, generally designated 12 (commonly called a heat exchanging chamber), and a collecting chamber, generally designated 13. In use, the oxygenating device may be suspended by hooks or other appropriate means passing through apertures 14 formed at opposite ends of the upper chamber 10. When in normal operation, the angle formed by the axis of the upper cylindrical chamber 10 with the horizontal is preferably in the range of approximately 35 to 40 degrees and, more specifically, 37 to 38 degrees.

The chambers 10, 11, 12 and 13 are preferably formed from a polycarbonate plastic (sold by General Electric under the trademark "Lexan") which may either be vacuum formed or injection molded to shape two self-sustaining substantially rigid shells 15 and 16 which are substantially identical to each other except one is the mirror image of the other. The two shells are each provided with a coplanar peripheral flanges 17, and the peripheral flanges of the two shells are adhered together by a suitable adhesive or other methods of bonding to form a unitary, transparent structure. The plastic is inert, nontoxic, impervious to the passage of gasses and liquids, and sterilizable. It contains no leachable plasticizers which may be traumatic to the blood, and it is exceptionally strong and durable in order to withstand accidental blows or shocks.

The upper structure or oxygenating chamber 10 comprises the bubbler assembly generally designated 18 of the instant invention, which bubbler assembly is preferably mounted so that its longitudinal axis substantially coincides with the longitudinal axis of the cylindrical chamber 10. The function generally of the bubbler assembly is to intermix oxygen gas with incoming venous blood so as to form films of blood in bubble form, which blood bubbles are advanced in an oxygen atmosphere through the bubbler assembly to an outlet. The oxygen atmosphere exists within each of the blood bubbles and the thin films of venous blood exposed to the oxygen effect a transfer of oxygen gas to the hemoglobin in the blood and the consequent release of carbon dioxide from the hemoglobin of the blood.

In effecting this oxygen-carbon dioxide exchange, it is particularly important that as many bubbles as possible of uniform size be formed, and that there be a thorough intermixing of blood bubbles into the passageway of the bubbler assembly and continuous movement of the blood bubbles throughout the entire passageway to avoid pooling in the passageway. Similar important is the control of the size of the blood bubbles as they progress through the passageway. The structure of the instant bubbler assembly has proven to be extremely efficient in this regard and has shown a capability of being able to maintain a desired physiological oxygen to carbon dioxide ratio at improved gas-blood flow ratios. The bubbler assembly has further shown a capacity effecting a substantial increase in the oxygenation of blood over the range of both high and low blood flow rates.

Figure 6:
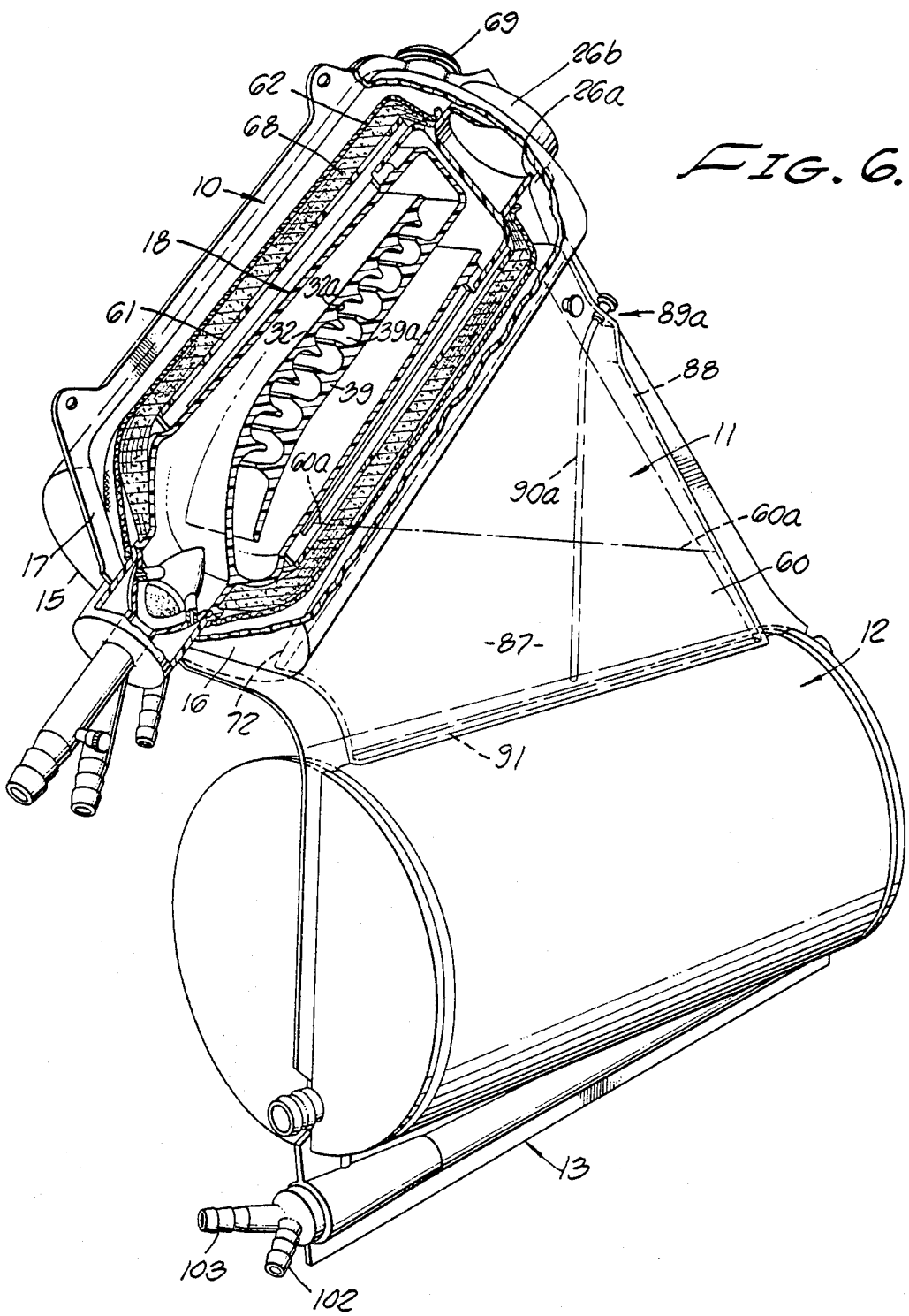
FIG. 6 is a side perspective view of an alternate embodiment of an oxygenating device according to the present invention, partially in section to illustrate the oxygenating chamber and heat exchange chamber.

The detailed structure of the bubbler assembly 18 is best shown in FIGS. 6 and 8 and all parts of the bubbler assembly are preferably formed from the polycarbonate plastic material referred to previously. Referring to FIG. 8, the bubbler assembly or column 18 includes a hollow, elongated housing, generally designated 19 and comprises generally bubbler or bubbling chamber 53 and a continuous closed mixing passageway 20. A closure plate 21 is disposed at one end of the bubbler assembly and carries venous blood inlet means, generally designated 22, and an oxygen inlet means, generally designated 23. The closure plate 21 has a peripheral flange 24 which is adhered to the lower end of the bubbler assembly housing 19 by suitable adhesive to provide an air-tight seal. The other end of the bubbler assembly housing 19 is covered with a cap or cover member, generally designated 25, which is removably mounted on four tabs, generally designated 25a, affixed circularly 90 degrees apart on the outside of the housing 19. The cover member preferably is generally circular shaped and is provided with an over-hanging portion 26, which is spaced outwardly of the sides of the housing 19 by the tabs 25a so as to afford an outlet opening 27 which extends 360 degrees around the housing 19 for blood and blood bubbles, generally designated 28. Such an outlet provides for improved flow through the bubbler assembly. The cap member 25, when positioned on the tabs 25a, is approximately one eighth of an inch from the uppermost portion 28 of the bubbler assembly 18. The housing 19 is partitioned so that a continuous closed mixing passageway 20 is divided into a plurality of passageway segments. An upper segment 30 is defined by a generally rounded upper wall 31 and a generally planar bottom wall 32 which extends from a bubbler chamber 53 at the inlet section 33 upwardly and rearwardly away therefrom to a downwardly returned rounded end portion 34. The interior surface 35 of portion 34 directs fluid from a downstream outlet end 36 of segment 30 into a juncture portion 37 by means of which upper segment 30 is in communication with a vertically adjacent mixing segment 38 where blood bubbles are uniformly mixed with free oxygen. The cross-sectional flow area of the passageway 20 which is relatively large at the inlet section 33 smoothly tapers inwardly or decreases as it extends to the outlet end 36 and through juncture portion 37. Fluid is further directed downwardly and forwardly by the segment 38.

Mixing segment 38 is defined by the undulate wall 32a, which is the reverse side of the generally planar wall 32, and an undulate lower wall 39a. In the preferred embodiments, each of the walls 32a and 39a is comprises of a series of arcuate sections or secondary flow-producing deflecting protrusions 38a in end-to-end relationship to provide a serpentine passageway. As the blood bubbles pass through the serpentine passageway, they are subjected to secondary flow which substantially increases the efficiency of the oxygen-carbin dioxide exchange. The secondary flow is a gently swirling or rotating flow of blood bubbles. Secondary flow is imparted to the stream of blood bubbles as they pass through the rounded portions of the arcuate sections comprising the serpentine passageway. The blood bubbles are, thus, continually swirling and rotating as they flow through the length of the serpentine passageway. This gentle turning or rotating of blood bubbles significantly facilitates oxygenation of the blood. Segment 38 extends from its juncture 37 at the rear in communication with upper segment 30 to a forward outlet end 40 where it joins with a lower segment 41. The cross-sectional flow area of passageway 20 first increases slightly as it extends from its upstream inlet end at the juncture 37 to a midsection 41a and then decreases as it extends toward the outlet 40. The interior surface 42 of rounded end portion 43 directs fluid through a juncture portion 44 by means of which segment 38 communicates with segment 41. Outlet end 40 and, more particularly, juncture portion 44 defines a section of the passageway 20 having reduced or restricted cross-sectional flow area which is slightly smaller than the cross-sectional flow area of the passageway 20 at the outlet 36 and juncture portion 37. Fluid is returned rearwardly of segment 41 by the interior surface 42 of rounded end portion 43. Lower segment 41 leads away from its juncture at 44 with mixing segment 38 to the outlet means 27 remote from the inlet section 33. Lower passageway segment 41 is defined by the generally planar wall 39, which is the reverse side of the undulate lower wall 39a, and a generally rounded bottom wall 46. The cross-section flow area of the passageway 20 in the lower segment 41 increases as it extends from the juncture 44 to provide for a relatively large and unrestricted cross-sectional flow area throughout the length of segment 41.

Thus, blood entering generally through the inlet area will travel an inverted S-shaped path first passing through the upper segment 30, thence being directed downwardly and returned forwardly through the mixing segment 38 and thence being directed upwardly and returned rearwardly through the lower segment 41 from which it is passed outwardly through outlet means 27. In the sections of the passageway 20 where cross-sectional flow area is decreased, the flow is accelerated therein to insure continuous flow throughout the bubbler assembly and, thereby, reduce pooling. Moreover, the variations of the cross-sectional flow area of the passageway 20 control the size of the blood bubbles as they flow through the bubbler assembly. That is, the blood bubbles are the smallest when first formed at the bubbling section where the pressure acting on the blood bubbles, as a result of the downstream bubbles above, is greatest. As the blood bubbles progress upwardly in the passageway segment 30, the pressure decreases and the size of the bubbles increases. However, as the cross-sectional flow area of the passageway 20 decreases the flow therethrough is constricted and the bubble size is again reduced. Thus, the pattern of the bubble size as the bubbles progress through the bubbler assembly is such:

Bubble size is the smallest when the bubbles are first formed in the bubbling section 33; bubble size increases as the blood bubbles begin to progress upwardly in the segment 30; bubble size decreases as the blood bubbles move to and through the outlet 36 and juncture 37; bubble size increases as the blood bubbles progress through the segment 38 from the juncture 37 to the mid-section 41a of the segment 38 and then decreases as the blood bubbles progress to and through the outlet end 40 and juncture 44; and, finally, bubble size increases as the blood bubbles progress from the juncture 44 through the segment 41 to the outlet means 27.

It is believed that due to the fact that the atmosphere, within the device comprises more oxygen than carbon dioxide, blood bubbles more readily accept oxygen on the surface of the bubble and more readily dissipate carbon dioxide into the interior of the bubble. Thus, it is believed that the larger bubbles dissipate carbon dioxide more efficiently and the smaller bubbles oxygenate more efficiently. Therefore, this control of the bubble size, and in particular the variations of bubble size as the blood bubbles progress through the passageway 20 is considered to be very important in effecting the desired gas-blood transfer.

At the inlet section 33, is bubbling chamber 53, which includes a cone-shaped wall member 50 that supports a generally egg-shaped diffusion cone 51 by three legs 51a. The legs 51a are hollow and provide a passageway from the exterior of the cone-shaped wall member 50 to the interior of the diffusion cone 51 for oxygen which is introduced into the area between the cone-shaped wall member 50 and the closure plate 21 by way of the oxygen inlet means 23. The legs 51a are formed as part of the top portion 51b of the diffusion cone 51, this top portion being constructed of polycarbonate plastic. Bonded to the top portion 51b is the bottom portion 51c of the diffusion cone which is formed of porous polyethylene material available commercially as "Porex" high density polyethylene from the Porex Division of Glasrock Products, Inc., with a plurality of minute apertures 51d through which oxygen is admitted into the housing 19. This material is prepared by sintering particles of polyethylene to produce a porous structure having relatively uniform pore sizes. Other plastic materials such as polypropylene and polyvinylidene fluoride can be processed in the same manner as described in the brochure "Porex Porous Plastics for Industry, Science and Medicine", which is incorporated by reference herein. The pore size may vary, with 10-30 microns being suitable and 20 microns preferred. Alternatively, perforated members, e.g., of the type disclosed in U.S. Pat. Nos. 3,488,158 and 3,578,411 may be used.

Figure 11:
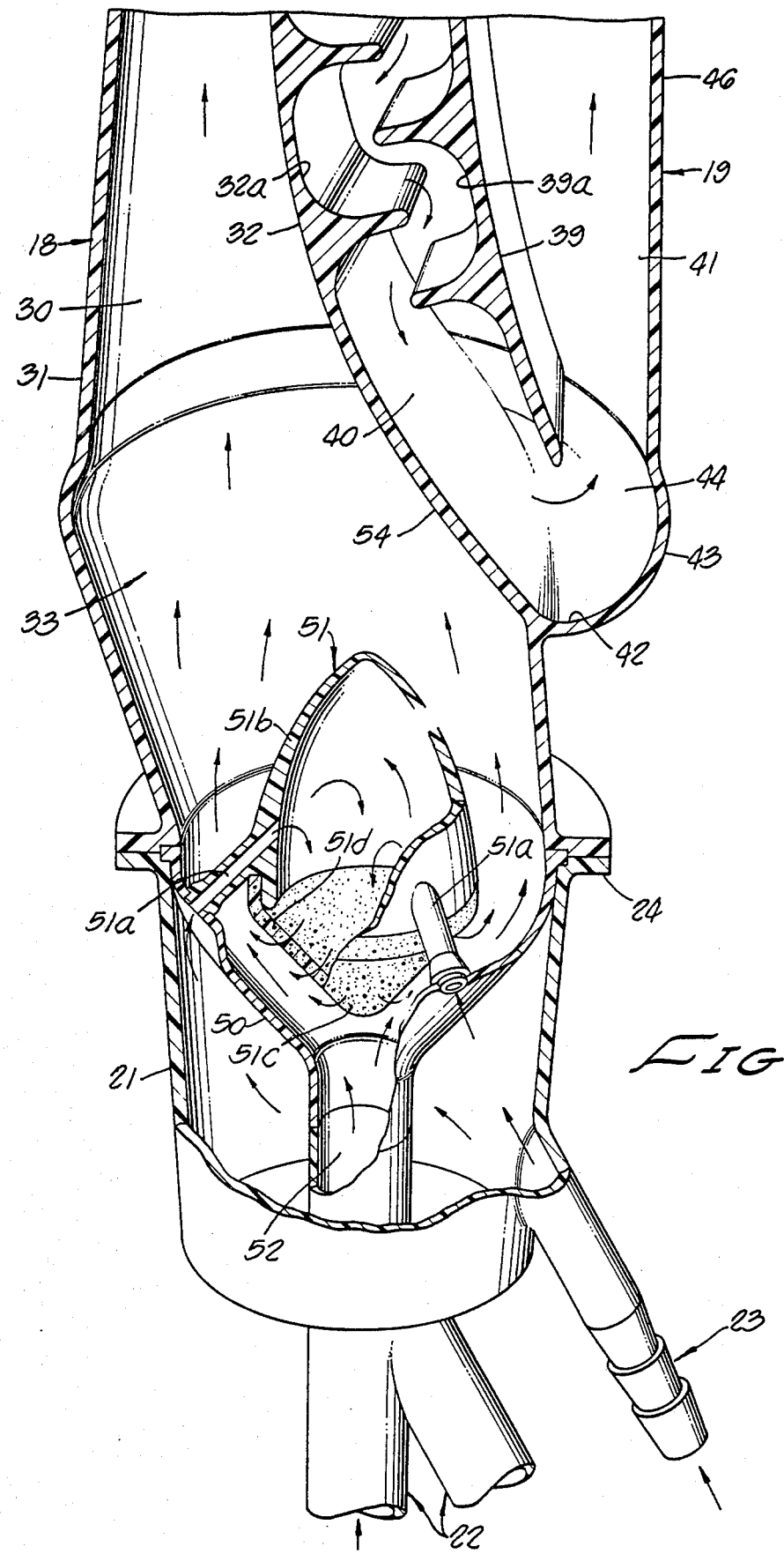
FIG. 11 is a perspective view of the bubbler chamber and the diffusion cone of the device of FIG. 6 illustrating the flow of blood and oxygen into the bubbler chamber and the formation of blood bubbles.

As can be seen in FIG. 11, the inner diffusion cone is centrally disposed within chamber 53 and the inner surface of the cone-shaped wall member 50 provides a divergent mouth for the inlet port 52 of the blood inlet means 22 and the bottom portion 51c directly opposes the inlet pore 52. As venous blood flows out of the inlet port 52, the laminar flow thereof is disturbed and secondary flow or tubulence is induced. The blood is uniformly distributed around the diffusion cone 51 and immediately bubbled by the multitude of tiny jetting streams of oxygen pointed directly into the flow of blood. By constructing the bottom portion of the diffusion cone out of Porex porous polyethylene, bubbles of small diameter, as well as relatively uniform bubbles, can be formed. The location and structural arrangement of the diffusion cone provides not only for uniform distribution of incoming venous blood so that substantially all of the incoming blood is quickly formed into bubble films with effective rapid exposure of the blood in film form to an oxygen atmosphere, but also for the uniform distribution of bubbles blood flowing into the continuous closed mixing passageway 20. The number of bubbles formed, the uniformity of the bubbles, and the flow distribution of the incoming venous blood, as well as the bubbled blood passing into the closed passageway, all, individually and in combination, significantly contribute to a more efficient oxygenation process.

Although the above-described structure is preferred for combining the incoming blood and oxygen, a porous or permeable membrane may be used or the porous plastic may be provided with such a membrane on its outer surface to achieve greater uniformity of bubble size.

Still further, the diffusion means may be of virtually any configuration, e.g., conical, tubular, etc., but it is believed that the embodiment shown in the drawings results in a high degree of efficiency with minimum risk of blood damage.

In the embodiments shown, a venturi effect is created as the incoming blood pases around the diffusion cone.

As seen in FIG. 8, the housing 19 is upwardly inclined when in operative working position. The blood bubbles initially formed in the bubbler chamber 53 are guided upwardly by inclined surface 54 into the upper passageway segment 30. Within segment 30 some bubbles may burst and reform droplets of blood, while still other small quantities or droplets of blood may be carried along in the upward progress of the bubbled blood in the segment 30. However, as droplets of blood form, the droplets gradually gather together and flow back downward by gravity into the bubbler chamber 53 once more where the blood is again rebubbled and moved once more up the passageway segment 30.

As the blood bubbles pass through the outlet means 27 of the bubbler assembly 18, the bubbles flow down the outside of housing 19 to liquid blood reservoired in the oxygenating chamber 10. The level of this reservoired blood is identical to that in the blood reservoir 60 of the central chamber 11 and is approximately indicated by the phantom line 60a shown in FIG. 6. Some of the bubbles may dissipate and form droplets of blood as they flow down the outside of housing 19, while other bubbles may dissipate as they contact the liquid debubbled blood reservoired around the outside of the lower end of the oxygenating chamber.

Referring to FIGS. 6 and 10, situated on the outside of the bubbler assembly 18 is a defoamer support means 61 which provides the space between the bubbler assembly 18 and defoaming means 62 for the blood bubbles to freely pass from the outlet means 27 to the reservoired blood. This defoamer support means 61 is preferably constructed of polypropylene in a lattice-work fashion, having a plurality of spacing segments 63 parallel to each other and a plurality of holding bands 64, which are parallel to each other, but affixed to the spacing segments 63 perpendicular thereto with such holding bands 64 fixedly positioned at each end of the spacing segments 63. Certain of the holding bands 64 are longer than others and have pins 64a affixed to ends thereof, which extend radially out from the longitudinal axis of the chamber 10, and holes 64b in the other ends to accommodate said pins 64a. This arrangement allows for the defoamer support means to be fastened into place when wrapped around the outside of the bubbler assembly 18 by snapping the pins 64a into the holes 64b.

As shown in FIG. 9, the spacing segments 63 are preferably so constructed as to have one side which incorporates a seating extension 65 at one end and a cap indentation 66 at the other end. The other three sides of the spacing segments 63 are flat and the holding bands 64 lie across the flat side of each spacing segment 63 opposite the seating extensions 65 and the cap indentations 66.

As shown in FIG. 10, the defoamer means 61 is wrapped around the bubbler assembly 18 with the spacing segments 63 running parallel to its longitudinal axis and with the holding bands 64 circumscribing the bubbler assembly 18 perpendicular to its longitudinal axis. The only portions of the defoamer support means 61 that contact the bubbler assembly housing 19 are the seating extensions 65, which do so at the lower end of the bubbler assembly housing 19 at a bulging portion 67 thereof, which provides a restricing surface upon which the seating extension 65 rests, holding the defoamer support means 61 in its desired position relative to the bubbler assembly 18. The cap indentations 66 at the upper end of the defoamer support means 61 provide an opening whereby the cap member 25, which covers the top of the bubbler assembly 18, can be placed in its operating position between the defoamer support means 61 which extends to approximately the top wall 25b of the cap member 25 when the oxygenating chamber 10 is in its fully assembled configuration.

The defoamer support means 61 is held in position around the bubbler assembly 18 by the defoaming means 62, which it supports away from the bubbler assembly housing 19 approximately one half inch. The defoaming means 62 is preferably formed in the shape of a sleeve which is open at both ends, fits over the outer lateral surface of the defoamer support means 61 and has a draw string at its lower open end which is drawn tightly around the bubbler assembly 18 so that all the blood flowing out of the bubbler assembly 18 will be caused to flow through the defoaming means 62. The upper portion of the bag when fitted over the defoamer support means 61 fits snugly around a cylindrical segment 26a of the cap member 25 which connects with the top wall 25b of the cap member 25 and extends out therefrom. This arrangement affords a window so that an operator of the oxygenating device can see that blood bubbles are being formed properly. The sleeve is constructed of a plurality of similarly shaped sleeve layers 68 of knitted mesh material, which layers are nested one within another to provide a multitude of tortuous paths of flow. The knitted layers 68 are preferably formed of polypropylene fibers (polyurethane foam also being acceptable) each of which is generally smooth and round and presents no rough surfaces (which may cause damage to the red cells) to the flow of blood passing therethrough. The polypropylene layers 68 are impregnated or coated with a non-toxic antifoam composition of the medical silicone antifoam type which is well known in the art.

Thus, as blood bubbles collect on the surface of the reservoired blood and move outwardly on the surface, they contact the defoaming layers, reducing the surface tension of the bubbles which dissipates them, and rivulets of oxygenated blood are formed, freeing excess oxygen and carbon dioxide which escape the bubbler assembly via outlet means 27, then pass through the defoaming means 62 and a porous bag 70 which surrounds the defoaming means, and finally exit the oxygenating chamber 10 through port 69 (shown in FIG. 6) provided for such purpose near the top of the oxygenating chamber. The same is true for any blood bubbles that might contact the defoaming means 62 before reaching the blood bubbles that might contact the defoaming means 62 before reaching the blood reservoired in the oxygenating chamber within the defoaming mens.

As shown in FIG. 10, a porous bag 70 covers the defoaming means 62 in the same way that the defoaming means covers the defoamer support means 61, but has drawstrings at both its open ends, which are drawn tightly around the bubbler assembly 18 and cap member 25 so that all the blood and gas flowing out of the bubbler assembly 18 will be caused to pass through the bag 70. This bag 70 aids in holding the defoaming means 62 in its shown configuration. Also, the bag 70 preferably formed of nylon material and having a pore size of about 150 microns, filters blood as it exits the bubbler assembly 18. In the adult size oxygenator, the bag 70 preferably has a surface area of approximately 144 sq. in. Also, in the adult size oxygenator, it is preferred to provide about 4 or 5 layers 68 of the polypropylene mesh, while in the pediatric and infant size the number of layers may be decreased.

Between the defoaming means 62 and the porous bag 70, a polyethylene sheet 71 is positioned so as to extend about the bottom of the bubbler assembly 18 for nearly 120 degrees. The arcuately disposed lower marginal edge of the polyethylene sheet 71 is normally positioned about four inches upwardly of the lower end of the oxygenating chamber 10, and the upper arcuate marginal edge of the sheet 71 extends beyond the cap member top wall 25b. This sheet 71 is fastened to the defoaming means 62 by tack-like buttoners 71a which have barbed ends that pass through the sheet 71 and extend into the defoaming means 62. The polyethylene sheet 71 constitutes a troughlike formation for directing the flow of any debubbled blood passing through the defoaming means 62 before reaching the reservoired blood in the oxygenating chamber 10. This sheet 71 causes such debubbled blood to flow angularly downwardly through the defoaming means 62 within the sheet 71, helping to maximize the debubbling operation, and causes the blood to gradually flow to the lower end of the oxygenating chamber 10 so as to make a smoother exit therefrom through exit opening 72 (shown best in FIG. 6). Normally, debubbled blood is collected just past opening 72 and if sheet 71 were not present, some of the debubbled blood from the oxygenating chamber 10 might drip down and splash on such collected blood, causing undesirable bubbling.

As best seen in FIG. 6, the bubbler assembly is centered with respect to the oxygenating chamber and held away from the interior surfaces thereof by the cylindrical segment 26a of the cap member 25 fitting within cylindrical indentation 26b of the upper wall of the oxygenating chamber 10. This configuration enhances the stability of the bubbler assembly arrangement over previous arrangements in which the bubbler assembly was cantilevered by its lower end and substantially reduces the possibility of the bubbler assembly leaking due to being jarred in handling or floating during the operation.

The narrow central or intermediate chamber 11 provides the reservoir 60 for the oxygenated blood. This central chamber has sidewall portions 87 (only one of which is shown) which are generally rather closely spaced and taper towards each other as they extend both from the oxygenating chamber 10 to the heat exchanging chamber 12 and from the top end of the oxygenating chamber to the bottom end thereof. The sidewall portions 87 round together from the lower end of the oxygenating chamber 10 to the heat exchanging chamber 12 and do the same thing from the upper end of the oxygenating chamber to the heat exchanger. However, due to the greater distance between the sidewall portions 87 essentially the entire way from the upper end of the oxygenating chamber to the heat exchanger, their rounding together forms a "V"-shaped back wall 88 to the central chamber 11 with the flange 17 running down its center.

In use, the lower end of the central chamber or reservoir 11 accommodates a small volume of oxygenated blood relative to the upper end and will fill rather rapidly so that the level of the blood will preferably extend into the lower end of the upper oxygenating chamber 10. This double-tapering structure allows for less priming liquid to be used in the start-up of the oxygenator than is required with the units described in the patents and pending applications listed earlier. This reduction in the needed volume of priming liquid makes the oxygenation process more physically acceptable to the patient when liquids other than his own blood are used for priming since the less liquid (not the blood of the patient) used the more acceptable the process to the patient, and helps afford better oxygenation when mixtures of blood and solutions for hemo-dilution are used, since blood alone is more readily oxygenated than blood mixtures and the smaller volume of such mixtures used the the better the oxygenation.

This double-tapering structure also provides for uniform blood flow through the central chamber 11, which substantially reduces the possibility of platelets collecting on the sidewall portions 87. The reason this structure provides for uniform flow stems from the fact that in its operating position the oxygenator is in an inclined position as discussed earlier and due to this inclination, blood tends to flow through the central chamber 11 more rapidly at the front, i.e., the portion nearest the inlet means 22, thereof when the cross-sectional flow area across a horizontal plane of the central chamber is uniform from front to back. By incorporating the structure just described, the cross-sectional flow area across a horizontal plane decreases in the central chamber proceeding from front to back which neutralizes the tendency for greater flow rates to exist nearer the front of the chamber and allows for the uniform flow that is advantageous from the standpoint of reducing the collection of platelets on the sidewall portions 87 of the central chamber 11.

In operation, blood enters the oxygenating chamber 10 through blood inlets 22 and oxygen is fed into the oxygenating chamber through inlet 23. The blood and oxygen are intermixed and travel through the passageway in the interior of the bubbler assembly 18 and mixed, particularly, through upper segment 38, and finally, through the outlet means 27 defined by the cap member 25. After passing through this outlet, the blood passes outwardly and downwardly to the exterior of the bubbler housing 19 to the reservoired blood and through the defoaming means 62 and then into the central chamber 11.

In central chamber 11, the blood is held in a vertical generally sheet-like column and flows therefrom by means of opening 91 into the heat exchanging chamber 12 so that its temperature can be raised before return to the patient. From the heat exchanging chamber, the blood travels to the blood-collecting chamber 13 from which it may be returned to a patient through discharge ports.

Figure 12:
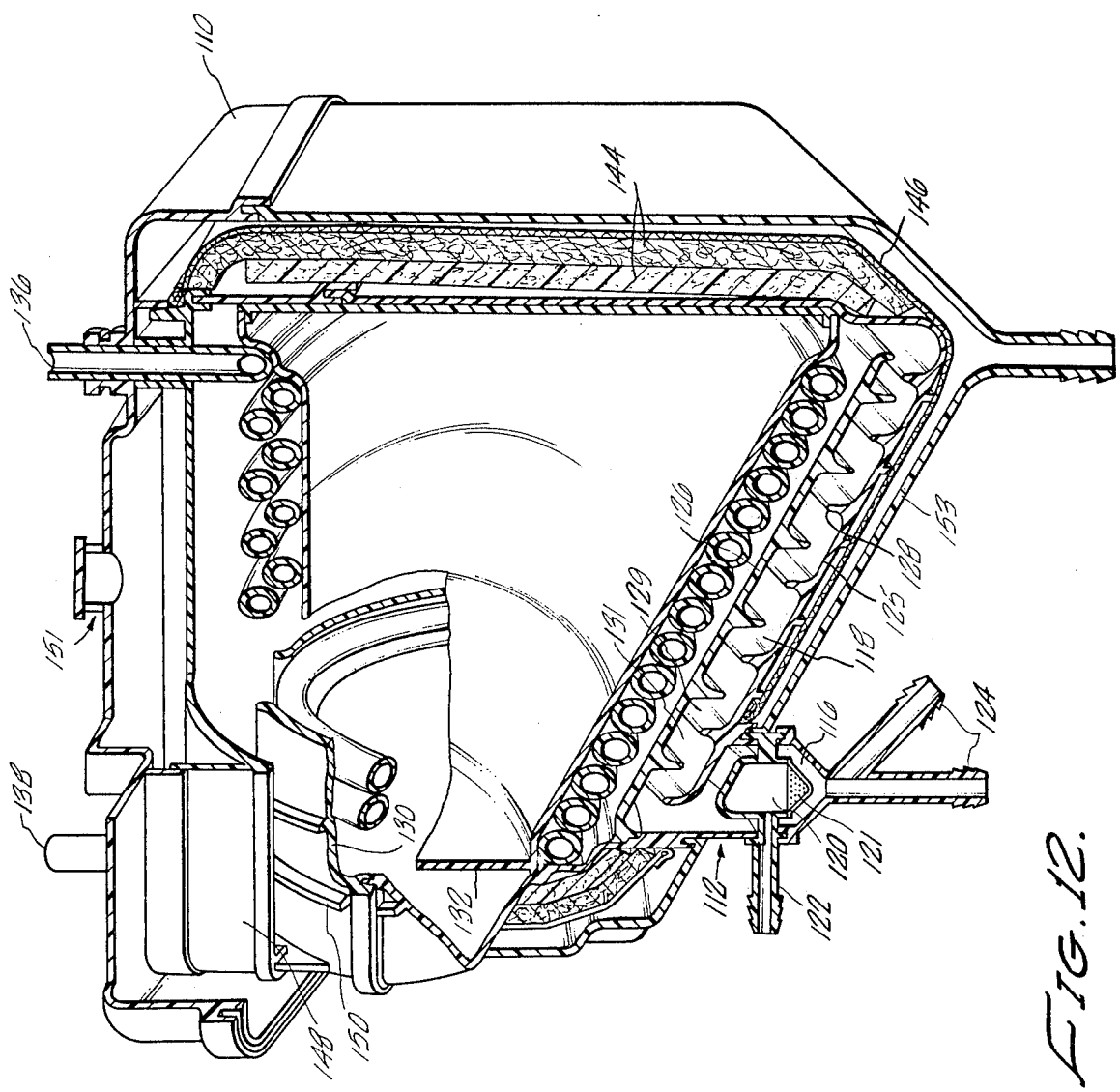
FIG. 12 is a perspective view, partially in section, of an alternate embodiment of an oxygenating device, according to the present invention illustrating the oxygenating chamber and the heat exchange chamber.
Figure 13:
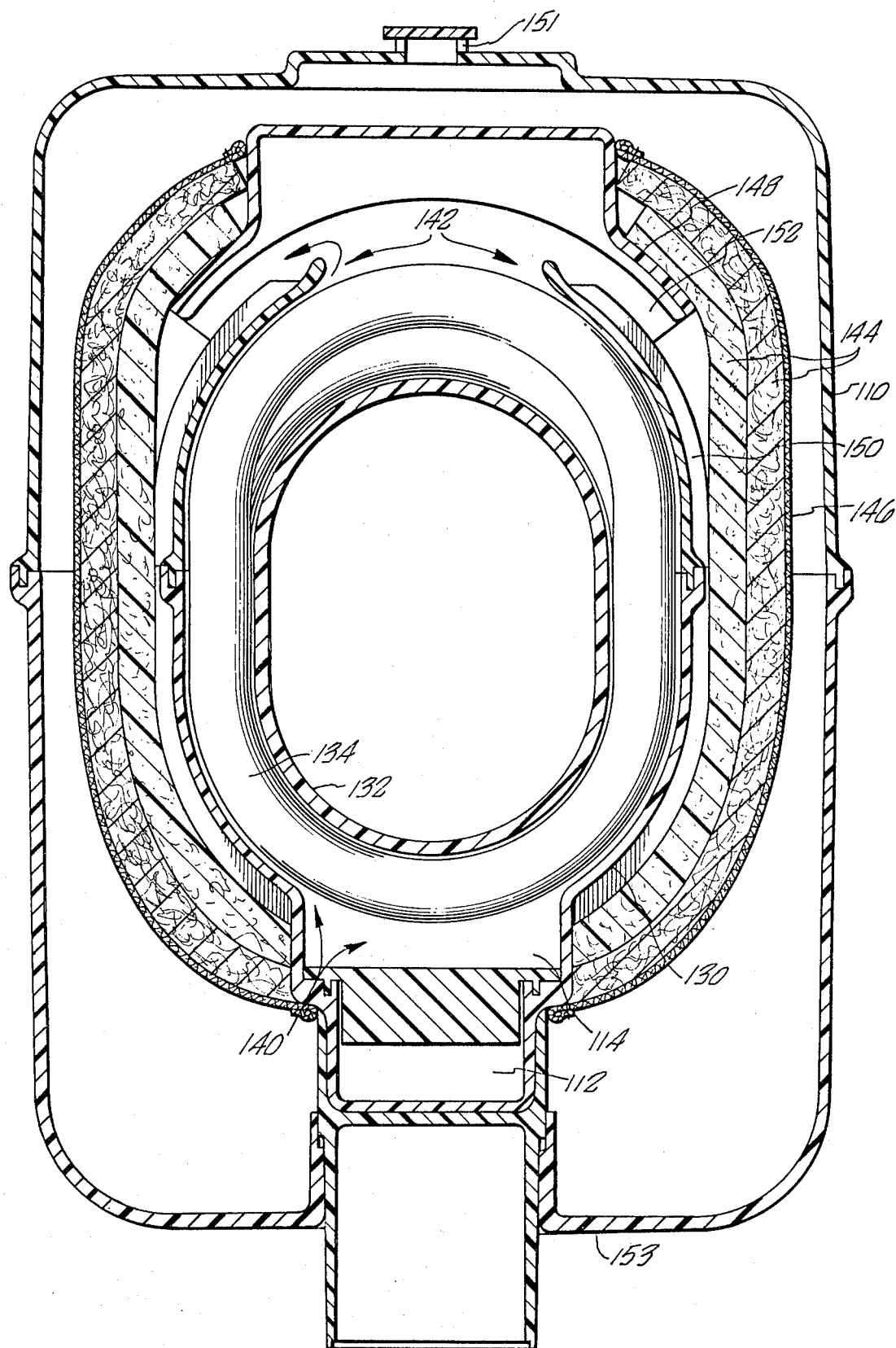
FIG. 13 is a cross-sectional view taken along line 13—13 of FIG. 12.

Referring to FIGS. 12 and 13, there is shown an alternate preferred embodiment of the blood oxygenator of the present invention. The oxygenator is generally comprised of outer housing 110 having disposed therein an oxygenating chamber 112 and a heat exchange chamber 114. The various parts of the oxygenator are also preferably comprised of polycarbonate material. The oxygenating chamber comprises generally bubbler chamber 116 and mixing passageway 118. The bubbler chamber is provided with a similarly formed diffusion cone 120 which is supported by oxygen inlet 122. The bottom portion 121 of the diffusion cone is preferably similarly comprised of a porous polyethylene having pore sizes from approximately 10 to 30 microns. The bubbler chamber is additionally provided with venous blood inlets 124 which open into the bubbler chamber 116. The diffusion cone is preferably similarly centrally disposed within the chamber 116 to disturb the laminar flow of entering blood. The diffusion cone so situated similarly enables the introduction of a substantial portion of oxygen into the bubbler chamber in a direction directly counter to the incoming flow of blood.

The mixing passageway 118 is similarly provided with upper and lower undulate walls 125 and 126 respectively, preferably extending along the entire length of the mixing chamber 118. The undulate walls 125 and 126 similarly comprise a series of arcuate secondary flow-producing deflecting sections or protrusions 128 which are positioned to form a serpentine passageway. The serpentine passageway similarly functions to cause secondary flow of blood bubbles as they pass therethrough. The cross-sectional flow area of the mixing passageway is similarly varied along its length to control the size of the blood bubbles. The arcuate protrusions 128 are offset so that the distance 129 between opposing arcuate protrusions is less than the distance 131 between successive opposing arcuate protrusions. The cross-sectional flow area is therefore successively increased and decreased along the entire length of passageway 118. This variation in cross-sectional flow area improves the oxygenating capabilities of the oxygenator.

The heat exchange chamber 114 is disposed within an inner housing 130 and is comprised of a generally frustrum-shaped enclosure 132 having a heating conduit 134 helically wound around the enclosure. The heating conduit is preferably formed from a thermally conductive metal having a biocompatible coating. The heating conduit is provided within inlet means 136 and outlet means 138. The wall of the inner housing 130 and the wall of the enclosure 132 define a narrow passageway 140 which contains the heating conduit and enables the blood exiting the mixing chamber 118 to flow up through the inner housing in close contact with the heating conduit. The thin film of the blood bubbles enables more efficient heat transfer from the heating conduits to the blood, thereby enabling more efficient regulation of the temperature of the blood. The top of the inner housing 130 is provided with a longitudinal slot 142 to enable the blood bubbles to exit the inner housing.

The defoaming means 144 is disposed around the outside of inner housing 130. The defoaming means is preferably similarly comprised of knitted polypropylene or, alternatively, polyurethane foam or combinations of foams and the defoaming means is preferably impregnated with a silicone antifoam composition. The defoaming means 144 is further provided with a similar porous bag 146 which is disposed around the outside of defoaming means and functions to support the defoaming means against inner housing 130. The bag 146 is provided with a drawstring which is secured to the outside of the oxygenating chamber 112 and to the downstanding flange 148 which is connected to outer housing 110. The defoaming means 144 is positioned around the outside of the inner housing 130 in such a manner that the blood bubbles passing out from slot 142 must pass through the defoaming means before existing housing 110, but the liquid blood simply flows down the outer surface of housing 130. The wall of inner housing 130 is preferably provided with a plurality of defoamer support tubes 150 which function to support the defoamer means 144 spaced apart from the wall of the inner housing, thereby similarly providing an open space 152 for the passage of blood bubbles exiting slot 142. The defoamer is also similarly provided with a polyethylene sheet disposed between the defoamer and the porous bag. The sheet functions as a trough to direct the flow of any debubbled blood within the defoamer.

In operation, the venous blood enters the housing through inlet 124 and oxygen enters the housing through oxygen inlet 122. The blood flows into bubbler chamber 116 and is immediately converted into blood bubbles as it passes by diffusion cone 120. The blood bubbles flow out of the bubbler chamber and up into mixing passageway 118. Upon exiting the mixing passageway 118, the blood bubbles flow up into the chamber formed by inner housing 130 through passageway 140 around the heating conduit 134. The blood bubbles exit passageway 140 through slot 142 formed in inner housing 130 and flow into open space 152 formed between the inner housing and defoaming means. The bubbles are dissipated by contact with the reservoired blood in space 152 or are forced into contact with the defoaming means, converting the bubbles into liquid blood and free oxygen and carbon dioxide gases. The free gases exit the housing through port 151 formed in the top of outer housing 110. The debubbled blood flows down the lower wall 153 of the outer housing and exits the housing through outlet 154.

As a result of this invention, blood oxygenators can effectively and efficiently transfer oxygen to blood at an improved gas-to-blood ratio while maintaining a desired physiological oxygen-to-carbon-dioxide ratio. In addition, this invention provides for enhanced bubbling and flow characteristics, which provides for more efficient oxygencarbon dioxide transfer and an overall more efficient oxygenating process, thereby permitting a lower gas-to-blood flow ratio which results in lower hemolysis levels. Further, this invention results in an oxygenator which allows for a reduction in the volume of priming liquid required for a start-up and operation of the unit.

What is claimed is:

1. Apparatus for oxygenating blood comprising: means for combining oxygen-containing gas with liquid blood to form a mixture of blood and gas, a substantial portion of said mixture being in the form of bubbles; means defining a flow path for the mixture; means in the flow path defining a passageway configured in a manner capable of imparting rotational movement to at least a portion of the bubbles, said passageway having a transverse dimension large enough to permit rotation of the bubbles; and defoaming means downstream of said passageway.

2. The apparatus of claim 1 wherein said apparatus is a hard-shell bubble oxygenator.

3. The apparatus of claim 1 wherein said means for imparting rotational movement comprises a flow-directing means having an undulate configuration.

4. The apparatus of claim 3 wherein said undulate configuration comprises a series of arcuate sections.

5. The apparatus of claim 1 including:
an inlet for the blood and an inlet for the oxygen-containing gas, both of which inlets are proximate to one axial end of said apparatus and to the beginning of said flow path; and
an outlet for oxygenated blood in the region of the other axial end of said apparatus and proximate to the end of the flow path.

6. The apparatus of claim 5 wherein said defoaming means is between the end of the flow path and the outlet for the oxygenated blood.

7. The apparatus of claim 5 wherein said means for imparting rotational movement include a helically wrapped tube in said flow path.

8. The apparatus of claim 7 wherein the outer surface of said helically wrapped tube is convoluted.

9. The apparatus of claim 8 wherein said tube is a heat exchanger tube.

10. Apparatus for oxygenating blood comprising: inlet means for liquid blood; inlet means for oxygen-containing gas; means for injecting said oxygen-containing gas into said blood to form a blood-gas mixture containing a substantial number of bubbles; passage means for conveying said blood-gas mixture containing a substantial number of bubbles away from said means for injecting; said passage means having a length substantially greater than its transverse dimensions; flow-directing means located along a substantial portion of the length of said passage means for imparting rotational movement to said bubbles; said flow-directing means forming at least one passageway having a transverse dimension sufficiently large to allow rotational movement of the bubbles; defoaming means located in the region of the end of said passage means remote from said means for injecting; blood outlet means; and means for venting gas from said apparatus.

11. The apparatus of claim 10 wherein said means for imparting rotational movement comprises a flow directing means having an undulate configuration.

12. The apparatus of claim 10 wherein said undulate configuration comprises a series of arcuately shaped elements.

13. The apparatus of claim 10 wherein said apparatus has a first end and a second end, said first end being at the opposite axial extremity of said apparatus from said second end; an inlet for the blood and a separate inlet for the oxygen-containing gas, both of which inlets are proximate to said first end and to the beginning of said flow path; and an outlet for oxygenated blood in the region of the second end and proximate to the end of the flow path.

14. The apparatus of claim 10 wherein said blood inlet and said blood outlet are axially spaced from each other, proximate to opposite axial ends of the apparatus.

15. The apparatus of claim 14 wherein said means for imparting rotational movement includes a helically wrapped tube.

16. The apparatus of claim 15 wherein said tube has convolutions on the outer surface thereof.

17. The apparatus of claim 15 wherein said tube is a heat exchanger tube.

18. The apparatus of claim 16 wherein said tube is a heat exchanger tube.

* * * * *